United States Patent [19]

Itoman et al.

[11] Patent Number: 5,665,086
[45] Date of Patent: Sep. 9, 1997

[54] INSTRUMENT FOR INSERTING AN INTRAMEDULLARY NAIL IN A BONE

[75] Inventors: Moritoshi Itoman, Kanagawa-ken; Satoshi Ojima, Tokyo, both of Japan

[73] Assignee: Asahi Kogaku Kogyo Kabushiki Kaisha, Tokyo, Japan

[21] Appl. No.: 446,572

[22] Filed: May 19, 1995

[30] Foreign Application Priority Data

May 20, 1994  [JP]  Japan ................................. 6-130986

[51] Int. Cl.⁶ ............................................. A61B 17/56
[52] U.S. Cl. ................................ 606/64; 606/98; 606/62
[58] Field of Search ..................... 606/57, 60, 62, 606/63, 64, 72, 86, 96, 98

[56] References Cited

U.S. PATENT DOCUMENTS

| | | |
|---|---|---|
| 4,781,181 | 11/1988 | Tanguy . |
| 4,881,535 | 11/1989 | Sohngen . |
| 5,034,013 | 7/1991 | Kyle et al. . |
| 5,057,110 | 10/1991 | Kranz et al. . |
| 5,128,146 | 7/1992 | Hirayama et al. . |
| 5,281,224 | 1/1994 | Faccioli et al. .................. 606/62 |
| 5,352,228 | 10/1994 | Kummer et al. .................. 606/64 |

FOREIGN PATENT DOCUMENTS 0548658  6/1993  European Pat. Off. .

*Primary Examiner*—Michael Buiz
*Assistant Examiner*—Mark S. Leonardo
*Attorney, Agent, or Firm*—Greenblum & Bernstein P.L.C.

[57] ABSTRACT

An intramedullary nail inserting and mounting instrument includes a base portion which can be mounted to one end of an intramedullary nail inserted in bone marrow of a pair of bone pieces of a fractured bone to be interconnected, a guide shaft portion which is integrally provided on the base portion and which extends in the direction of an extension of the intramedullary nail, a pressing member which is movable along the guide shaft portion to come into contact with one end of one of the bone pieces, and a pressing member moving device which moves the pressing member along the guide shaft portion. The disclosure also addresses a method for inserting and securing the intramedullary nail to the fractured bone using the mounting instrument.

19 Claims, 6 Drawing Sheets

5,665,086

INSTRUMENT FOR INSERTING AN INTRAMEDULLARY NAIL IN A BONE

BACKGROUND OF THE INVENTION

1. Field of the Invention

The present invention relates to an intramedullary nail (pin) mounting instrument which is used to connect fractured tubular long bones using an intramedullary nail.

If a long tubular bone, such as a femur or tibia, etc. is fractured, the fractured bone pieces are connected by an intramedullary nail to treat the same. FIGS. 10 and 11 schematically show the basic principle in the connection of fractured bone pieces using an intramedullary nail. In FIGS. 10 and 11, two separate bone pieces 101 and 103 of a fractured long tubular bone 1 are connected by an intramedullary nail 5 which is inserted in the bone marrow 3 of the bone pieces 101 and 103 whose inner ends 101A and 103A are opposed.

The intramedullary nail 5 is secured to separated bone pieces 101 and 103 by securing screws 9 which are screwed in both the cortical bones 7 of the bone pieces and the intramedullary nail 5, so that the fractured bones can be connected to be treated.

To effectively cure the fractured tubular bone 1, it is preferable, upon connection of the bone pieces 101 and 103, that the bone pieces contact each other at the inner ends 101A and 103A without stress.

However, in the known method as mentioned above, one of the bone pieces 101 or 103 is manually moved along the intramedullary nail 5 toward the other bone piece after the intramedullary nail 5 is inserted in the bone marrow 3 of the separated bone pieces, so that the opposed inner ends 101A and 103A of the separated bone pieces come close to each other. Therefore, the opposed inner ends 101A and 103A of the separated bone pieces 101 and 103 tend to be located slightly apart from one another. Namely, it is difficult for an operator to continuously hold the opposed inner ends 101A and 103A of the separated bone pieces 101 and 103 in close contact with each other.

SUMMARY OF THE INVENTION

It is an object of the present invention to provide a simple mounting instrument which can easily and certainly hold opposing inner ends of two separated bone pieces of a fractured bone in close contact when the bone pieces are interconnected by an intramedullary nail.

Another object of the present invention is to provide a method for inserting and securing the intramedullary nail to the fractured bone, using the mounting instrument.

According to an aspect of the present invention, there is provided an intramedullary nail inserting and mounting instrument, comprising a base portion which can be mounted to one end of an intramedullary nail inserted in a bone marrow of a pair of bone pieces of a fractured bone to be interconnected, a guide shaft portion which is integrally provided on the base portion and extending in the direction of an extension of the intramedullary nail, a pressing plate which is movable along the guide shaft portion to come into contact with one end of one of the bone pieces, and a pressing member which is movable along the guide shaft portion to come into contact with one end of the bone pieces and a means for moving the pressing member along the guide shaft portion.

Preferably, the base portion is provided with a drill guide which guides a drill which is adapted to pierce at least one preliminary hole in one of the bone pieces, corresponding to at least one threaded hole which is formed in advance in the intramedullary nail inserted in the bone pieces in a direction normal to the longitudinal direction of the nail.

The drill guide is preferably positioned such that said at least one preliminary hole is registered with the corresponding threaded hole of the intramedullary nail.

The pressing member moving means can be comprised of a male member which is screw-engaged by the base portion to extend in parallel with the guide shaft portion, said male member being rotatably connected at the front end thereof to the pressing member so as not to relatively move in the axial direction.

The pressing member moving means can be comprised of a threaded portion provided on the outer peripheral surface of the guide shaft portion and a threaded hole formed in the pressing member, so that the threaded portion of the guide shaft portion can be screw-engaged in the threaded hole of the pressing member.

The base portion can be comprised of a large diameter portion and a small diameter portion wherein the small diameter portion comprises the guide shaft portion.

Preferably, the base portion has a male screw member which is screw-engaged with the base portion wherein the male screw member is capable of being detachably engaged with the intramedullary nail.

According to another aspect of the present invention, there is provided a method for inserting and securing an intramedullary nail in the bone marrow of a pair of bone pieces of a fractured bone to be interconnected, comprising the steps of inserting the intramedullary nail in the bone marrow of the bone pieces to be interconnected; securing the intramedullary nail to one of the bone pieces; securing an intramedullary nail mounting instrument to the intramedullary nail within the bone marrow from the end of the other bone piece that is located away from the one bone piece; contacting the opposing ends of the bone pieces with each other by moving the other bone piece relative to the intramedullary nail toward the one bone piece using the intramedullary nail mounting instrument; and securing the other bone piece to the intramedullary nail.

The present disclosure relates to subject matter contained in Japanese patent application No. 06-130986 (filed on May 20, 1994) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENT

Figure 4:
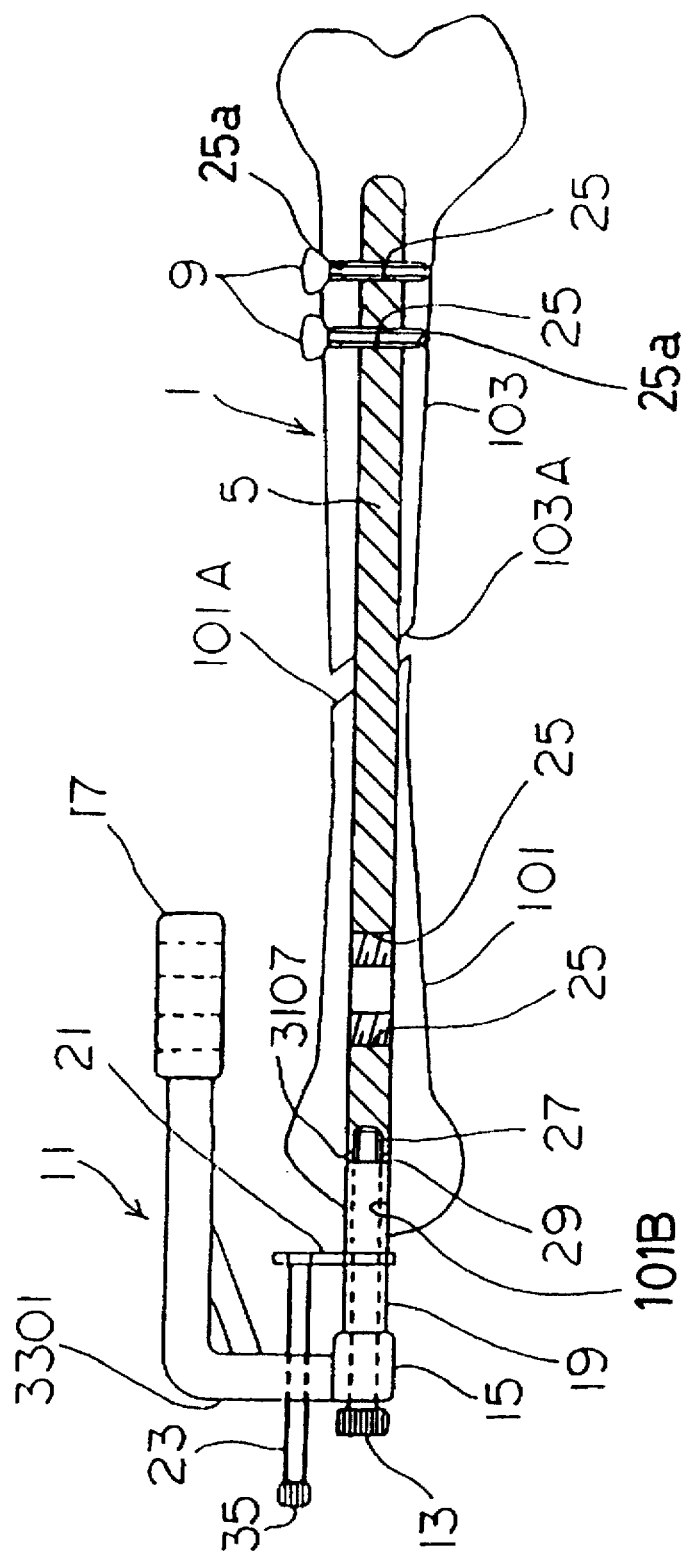
FIGS. 4, 5 and 6 are explanatory views of an intramedullary nail mounting instrument in different operative positions.
Figure 5:
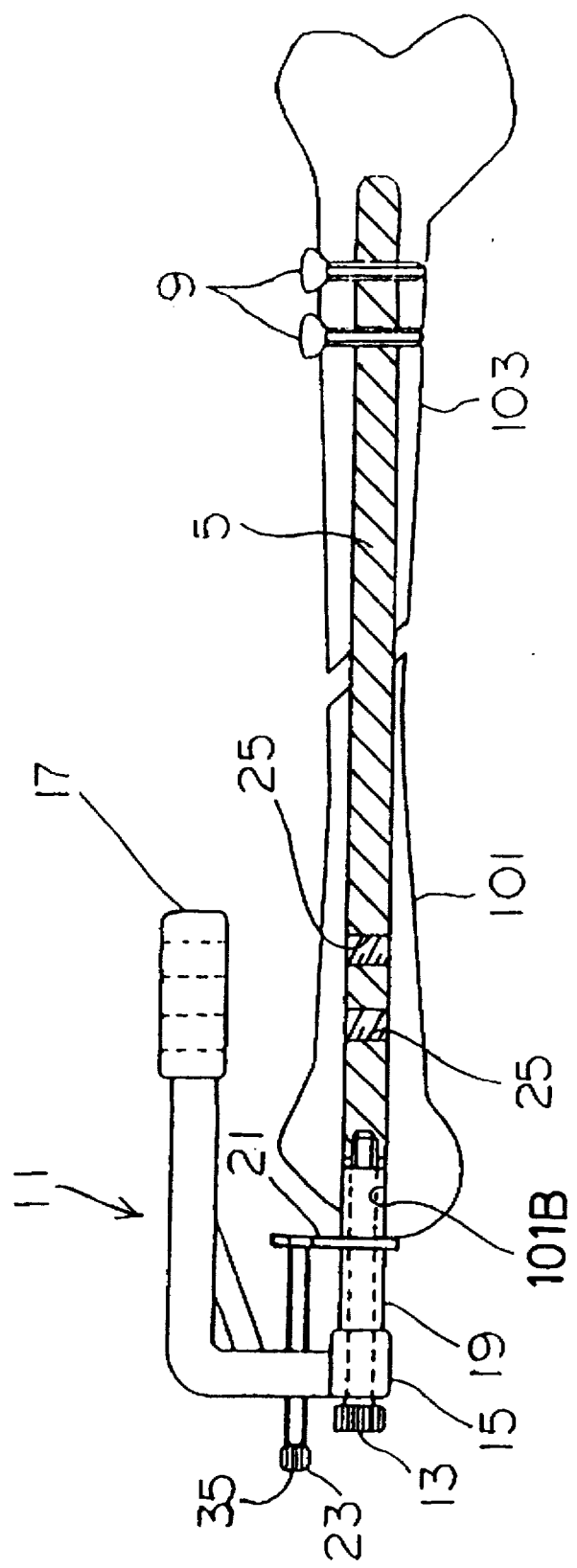
Figure 6:
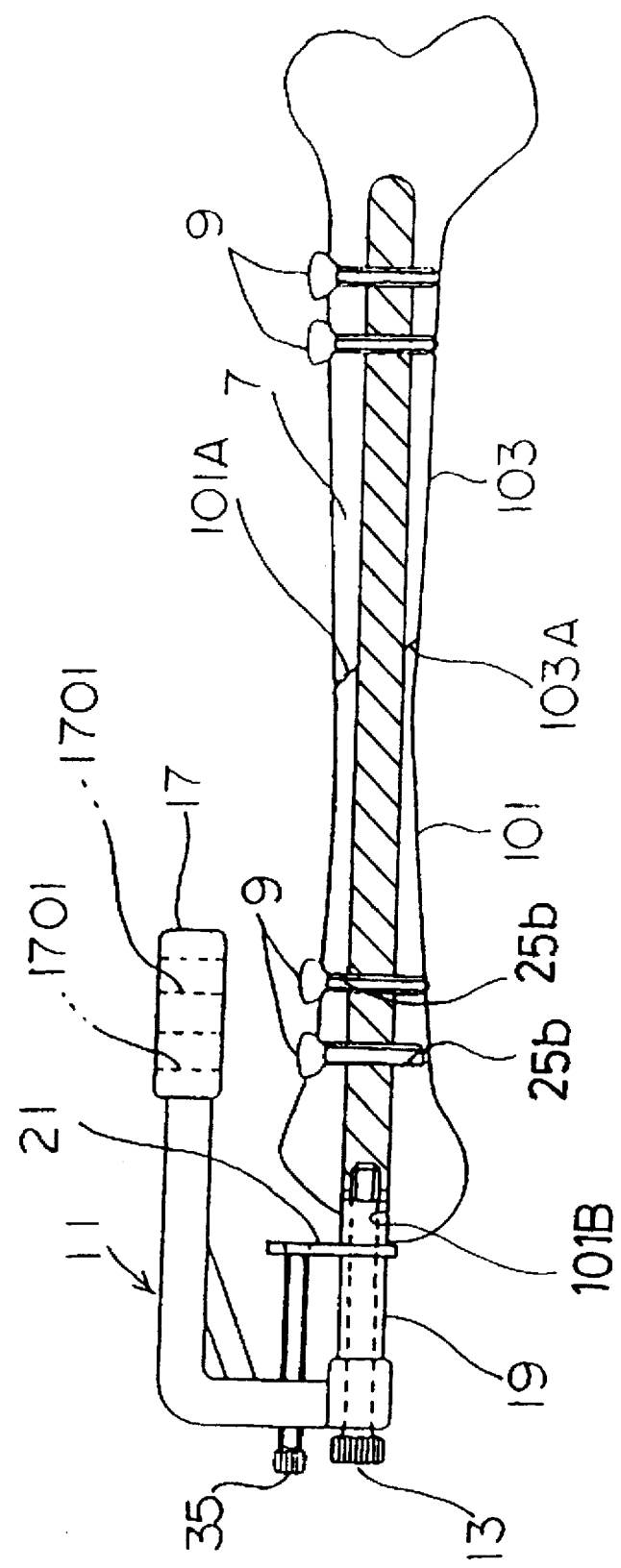

As can be seen in FIGS. 4 through 6, when a fractured long tubular bone 1 is treated, an intramedullary nail (pin) 5 is inserted in the bone marrow of separated bone pieces 101 and 103. To insert the intramedullary nail 5 in one of the separated bone pieces, for example, in the first bone piece 101, a hole 101B is pierced in the outer end of the bone piece 101, so that the intramedullary nail 5 is inserted in the bone marrow of the bone piece 101 through the pierced hole 101B. Thereafter, the intramedullary nail 5 is inserted in the bone marrow of the other bone piece (second bone piece) 103 through the inner end 103A thereof. After that, two screws 9 are screwed into the cortical bone of the bone piece 103 and the intramedullary nail 5 in the vicinity of the outer end of the bone piece 103 to secure the outer end of the bone piece 103 and one end of the intramedullary nail 5.

Thereafter, an intramedullary nail mounting instrument 11 according to the present invention is attached to the outer end of the intramedullary nail 5 located at the first bone piece 101. Consequently, the first bone piece 101 is moved close to the second bone piece 103 by the mounting instrument 11. Thereafter, two screws 9 are screwed into the cortical bone of the first bone piece 101 and the intramedullary nail 5 in the vicinity of the outer end of the first bone piece 101 to secure the outer end of the bone piece 101 and the other end of the intramedullary nail 5, as shown in FIG. 6. Thus, the bone pieces 101 and 103 are interconnected and returned to the original position.

The basic concept of the inserting and securing method of the intramedullary nail and the basic function of the mounting instrument can be briefly understood from the above discussion.

The aspects of a mounting instrument according to the present invention will be discussed below in detail.

Figure 1:
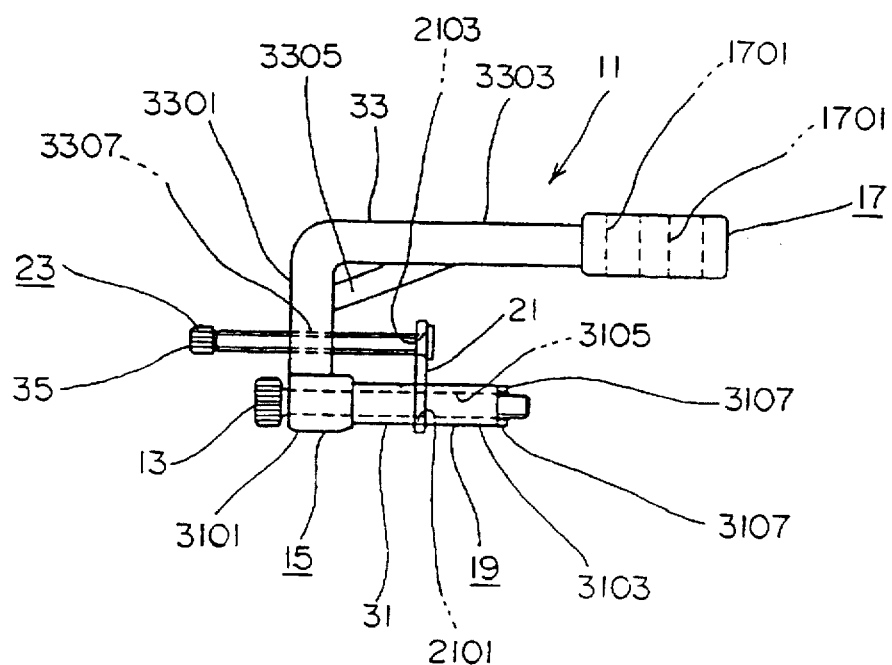
FIG. 1 is a front elevational view of an intramedullary nail mounting instrument according to the present invention.
Figure 2:
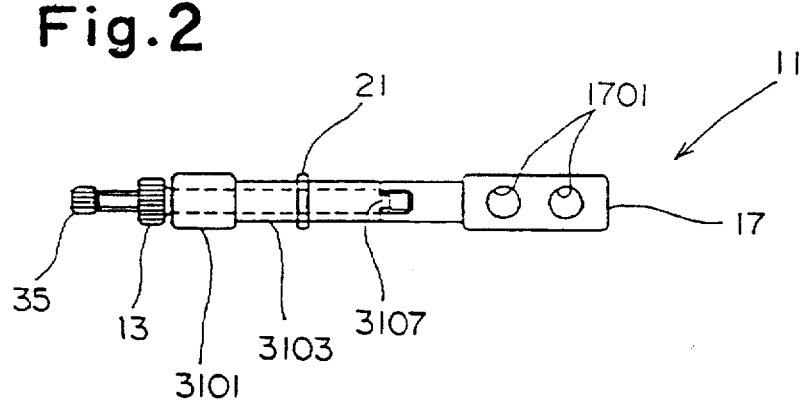
FIG. 2 is a bottom view of an intramedullary nail mounting instrument shown in FIG. 1.
Figure 3:
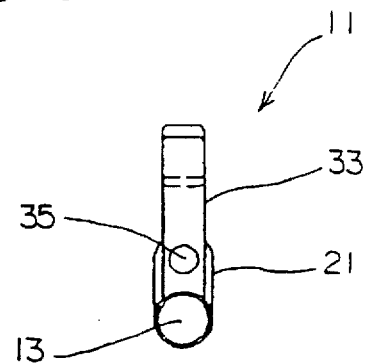
FIG. 3 is a side elevational view of an intramedullary nail mounting instrument shown in FIG. 1.

The intramedullary nail mounting instrument 11 includes a base portion 15 which can be mounted to the outer end of the intramedullary nail 5 by a male screw member 13, a guide portion 17 for inserting a drill which is adapted to pierce preliminary holes for the screws 9 in the bone pieces, a guide shaft portion 19 which extends in the length of the intramedullary nail 5, a pressing member 21 provided on the guide shaft portion 19, and a pressing member moving means 23 which is actuated to move the pressing member 21, as shown in FIGS. 1 through 3. The pressing member 21 presses and moves the first bone piece 101 toward the second bone piece 103.

The intramedullary nail 5 is provided with insertion holes 25 in which the screws 9 are inserted, a female screw portion (threaded hole) 27 on the outer end of the intramedullary nail 5, so that the male screw member 13 can be screw-engaged in the female screw portion 27, and a positioning recess 29 formed on the outer peripheral surface of the outer end of the intramedullary nail 5.

The base portion 15 includes a cylindrical member 31 and an arm 33 attached to the cylindrical member 31. The cylindrical member 31 is comprised of a large diameter portion 3101 and a small diameter portion 3103. An axial hole 3105 is formed in the large diameter portion 3101 and the small diameter portion 3103 and has an inner diameter large enough to insert the male screw member 13 so as to relatively rotate. The small diameter portion 3103 which has a predetermined axial length constitutes the guide shaft portion 19. The small diameter portion 3103 is provided on the front end thereof with a projection 3107 which can be fitted in the recess 29 formed on the outer end of the intramedullary nail 5.

The arm member 33 is comprised of a vertical arm portion 3301 which extends outward in the radial direction from the large diameter portion 3101, and a lateral arm portion 3303 which extends from the front end of the vertical arm portion 3301 in parallel with the longitudinal direction of the small diameter portion 3103. There is a reinforcing member 3305 extending between the vertical arm portion 3301 and the lateral arm portion 3303.

The vertical arm portion 3301 is provided on the intermediate portion thereof with a threaded hole (female screw portion) 3307 which extends in parallel with the guide shaft portion 19, so that a pressing bolt 35 which constitutes the pressing member moving means 23 is screw-engaged in the threaded hole 3307.

The guide portion 17 which is mounted to the front end of the lateral arm portion 3303 is provided with two guide holes 1701, that are spaced in the longitudinal direction of the lateral arm portion 3303, so that a drill can be inserted in the guide holes 1701. Note that the guide holes 1701 are constructed such that when the projection 3107 is fitted in the recess 29 of the intramedullary nail 5 and the front end surface of the guide shaft portion 19 abuts against the end surface of the intramedullary nail 5, the guide holes 1701 and the corresponding threaded holes 25 of the intramedullary nail 5 are respectively coaxially aligned.

The elongated pressing member 21 having a predetermined length which is provided, on the opposite ends thereof in the longitudinal direction, with holes 2101 and 2103. The guide shaft portion 19 is slidably inserted in the hole 2101, and the front end of the pressing bolt 35 is connected to the pressing member 21 while allowing relative rotation with respect to the other hole 2103. Namely, the pressing member 21 is moved together with the pressing bolt 35 in the axial direction thereof.

The surgical operation using the intramedullary nail mounting instrument 11 is performed as follows.

First, the inner ends 101A and 103A of the separated bone pieces 101 and 103 are opposed. Thereafter, the intramedullary nail 5 is inserted in the bone marrow of the bone pieces 101 and 103 from the outer end 101B of the first bone piece 101. After that, the screws 9 are screwed in the screw insertion holes 25 of the intramedullary nail 5 and the cortical bone of the second bone piece 103 in the vicinity of the outer end of the second bone piece 103.

To screw-in the screws 9 in the insertion holes 25, the position of the threaded holes 25 of the intramedullary nail 5 is confirmed by X-ray, and then, preliminary holes are formed in the cortical bone 7 by a drill, so that the preliminary holes 25a match with the corresponding insertion holes 25. Thereafter, the screws 9 are inserted in the preliminary holes 25a and screwed in the insertion holes 25 to secure the intramedullary nail 5 to the second bone piece 103.

Thereafter, the mounting instrument 11 is attached to the outer end of the first bone piece 101. Upon attachment of the mounting instrument, the male screw member 13 is inserted in the axial hole 3105 of the base portion 15, and the front end of the male screw member 13 is screw-engaged in the threaded hole 27 of the intramedullary nail 5, as shown in FIG. 4. When the male screw member 13 is tightened, the front end surface of the guide shaft portion 19 is pressed against the end surface of the intramedullary nail 5 while the projection 3107 is fitted in the recess 29. Note that the pressing member 21 is moved in advance adjacent to the vertical arm portion 3301 by the pressing bolt 35.

Thereafter, the pressing bolt 35 is rotated to move the pressing member 21 along the guide shaft portion 19 toward the outer end of the first bone piece 101. As a result, the end surface of the pressing member 21 abuts against the outer end of the bone piece 101, as shown in FIG. 5. Further rotation of the pressing bolt 35 causes the pressing member 21 to move together with the first bone piece 101 toward the second bone piece 103. As a result, the first bone piece 101 which is slid along and on the intramedullary nail 5 toward the second bone piece 103 comes into contact at the inner end 101A thereof with the inner end 103A of the second bone piece 103, as shown in FIG. 6.

When the inner end surfaces 101A and 103A of the first and second bone pieces 101 and 103, respectively, are in contact with each other, the rotation of the pressing bolt 35 is stopped. Thereafter, a drill (not shown) is successively inserted in the guide holes 1701 of the guide portion 17 to pierce the preliminary holes 25b for the screws 9 in the cortical bone 7 of the first bone piece 101 in a direction perpendicular to the longitudinal direction of the intramedullary nail 5, in the vicinity of the outer end of the bone piece 101.

Note that during the drill's piercing operation to form the preliminary holes 25b, the projection 3107 is engaged in the recess 29, and the front end surface of the guide shaft portion 19 abuts against the end surface of the intramedullary nail 5. Consequently, the guide holes 1701 and the corresponding axial holes 25 are aligned, and hence, the drill passes through the associated axial hole 25.

Thereafter, the screws 9 are inserted in the guide holes 1701 of the guide portion 17 and screwed in the axial holes 25 of the intramedullary nail 5 through the preliminary holes 25b thus formed in the cortical bone 7. Note that the preliminary holes 25b are formed in the cortical bone on both sides (upper and lower sides in FIG. 6) of the intramedullary nail 5.

After that, the male screw member 13 is rotated and disengaged from the end of the intramedullary nail 5, so that the mounting instrument 11 can be detached from the end of the first bone piece 101. Finally, the hole of the first bone piece 101 from which the guide shaft portion 19 has been removed is introduced with a bone compatible filler, thereby, completing the surgical operation.

According to the above-mentioned embodiment, not only can the mounting instrument 11 be easily attached to the end of the bone piece 101 by screw-engaging the male screw member 13 in the end of the intramedullary nail 5, but also the opposed inner ends 101A and 103A of the bone pieces 101 and 103 can be brought into contact with each other by rotating or fastening the pressing bolt 35 to move the bone piece 101 on the intramedullary nail toward the other bone piece 103.

Thus, the connection of the end surfaces 101A and 103A of the two bone pieces 101 and 103 can be easily performed by the above simple operation, thereby resulting in an effective treatment of the fractured bone.

Moreover, since the first bone piece 101 is moved by the rotation of the pressing bolt 35, a fine adjustment of the movement of the first bone piece can be effected. This makes it possible to easily and precisely bring the opposed inner ends 101A and 103A of the bone pieces 101 and 103 into close contact.

Furthermore, since the positioning of the drill for piercing the preliminary holes for the screws 9 is automatically effected by the guide portion 17, the screws 9 can be correctly engaged in the threaded holes of the intramedullary nail 5 through the corresponding preliminary holes, and hence, the bone pieces can be certainly and easily interconnected by the intramedullary nail 5 which is secured to the two bone pieces by the screws 9.

Figure 7:
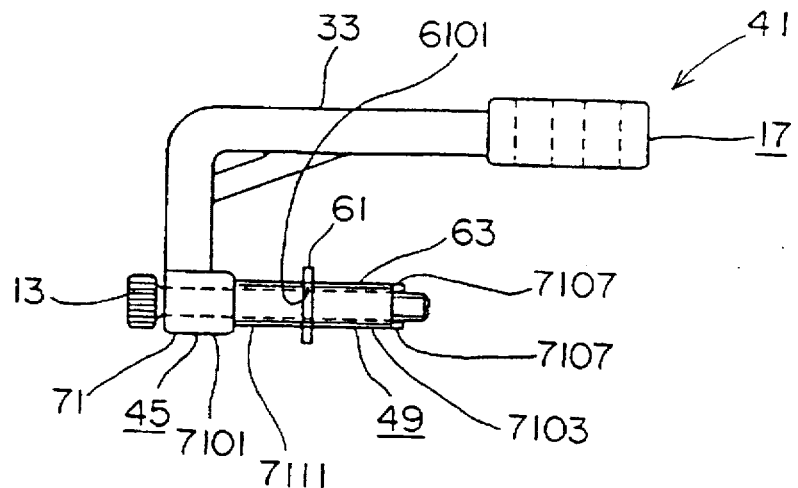
FIG. 7 is a front elevational view of an intramedullary nail mounting instrument according to another embodiment of the present invention.
Figure 8:
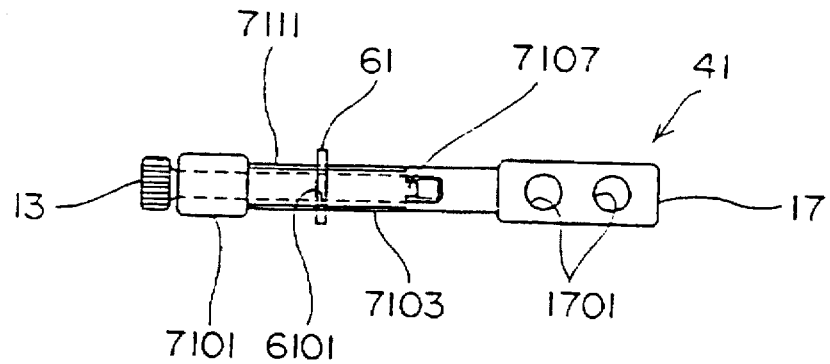
FIG. 8 is a bottom view of an intramedullary nail mounting instrument shown in FIG. 7.
Figure 9:
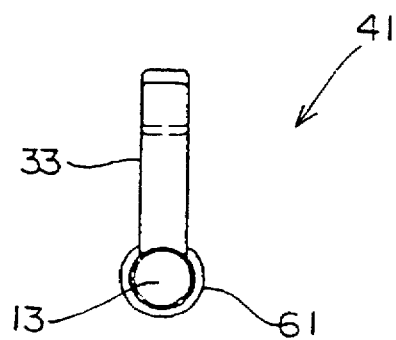
FIG. 9 is a side elevational view of an intramedullary nail mounting instrument shown in FIG. 7.
Figure 10:
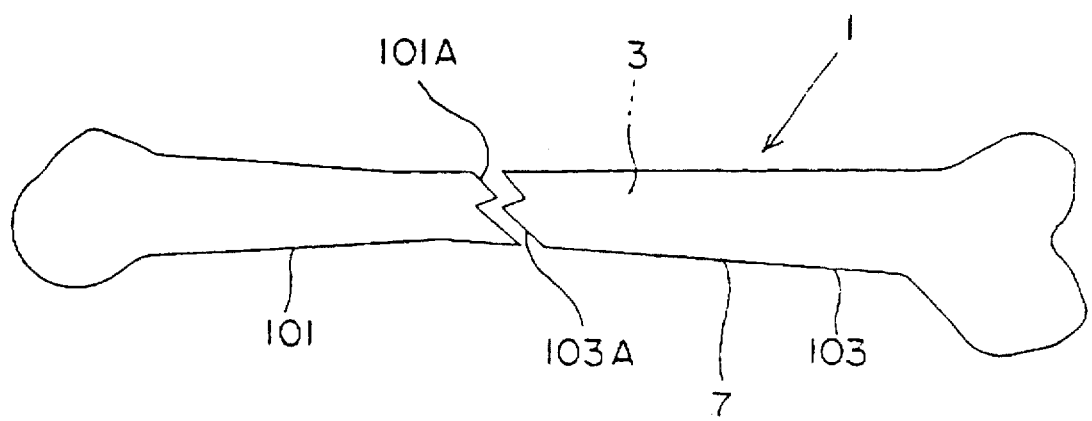
FIG. 10 is a front elevational view of a fractured long tubular bone.
Figure 11:
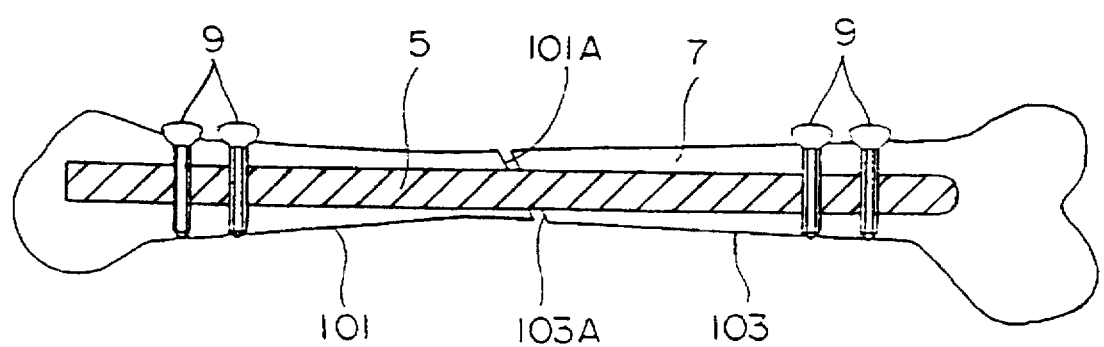
FIG. 11 is an explanatory view of a known connecting method of separated bone pieces of a fractured bone, using an intramedullary nail.

FIGS. 7 through 9 show a second embodiment of an intramedullary nail mounting instrument according to the present invention.

In the second embodiment, the elements identical to those in the first embodiments are designated with like reference numerals. The intramedullary nail mounting instrument 41 includes a base portion 45 which can be mounted to the outer end of the intramedullary nail 5 by a male screw member 13, the guide portion 17, a guide shaft portion 49 which extends along the length of the intramedullary nail 5, a pressing member 61 provided on the guide shaft portion 49, and a pressing member moving portion 63 which is actuated to move the pressing member 61.

The base portion 45 includes a cylindrical member 71 and an arm 33 attached to the cylindrical member 71, similarly to the first embodiment. The guide portion 17 is mounted to the front end of the arm 33. The cylindrical member 71 is comprised of a large diameter portion 7101 and a small diameter portion 7103. The attachment of the intramedullary nail mounting instrument 41 is carried out by tightening the male screw member 13 which is rotatably inserted in the cylindrical member 71 into the threaded hole 27 of the intramedullary nail 5, similarly to the first embodiment. The small diameter portion 7103 is provided on the front end thereof with a projection 7107 which can be fitted in the recess 29 of the intramedullary nail 5.

The small diameter portion 7103 which has a predetermined axial length is provided on the outer peripheral surface thereof with a male screw 7111. The circular pressing member 61 is provided with a female screw 6101 in which the male screw 7111 is engaged.

The pressing member 61 is supported by the base portion 45 when the male screw 7111 of the small diameter portion 7103 is screw-engaged in the female screw 6101 of the pressing member 61. When the pressing member 61 is rotated, the axial movement of the pressing member 61 occurs in the longitudinal direction of the small diameter portion 7103, so that the first bone piece 101 is moved toward the second bone piece 103 on and along the intramedullary nail 5. Consequently, in the second embodiment, the small diameter portion 7103 constitutes the guide shaft portion 49, and the threaded portions (male screw and female screw) 7111 and 6101 of the small diameter portion 7103 and the pressing member 61 constitute the pressing plate moving portion 63.

In the second embodiment, the inner ends 101A and 103A of the first and second bone pieces 101 and 103, respectively, are brought into close contact by simply rotating the pressing member 61. Furthermore, a fine adjustment of the movement of the first bone piece 101 can be effected, thus resulting in an effective treatment of the the fractured bone, as expected in the first embodiment.

We claim:

1. An intramedullary nail inserting and mounting instrument comprising:

a base portion which can be mounted to one end of an intramedullary nail, the intramedullary nail being inserted in the bone marrow or the pair of bone pieces of a fractured bone to be interconnected;

a guide shaft portion integrally provided on said base portion and extending in a direction of extension of the intramedullary nail;

a pressing member which is movable along said guide shaft portion to contact one end of one of the bone pieces; and means for moving said pressing member along said guide shaft portion said pressing member moving means comprising a threaded portion provided on an outer peripheral surface of said guide shaft portion in a threaded hole formed in said pressing member, so that said threaded portion of said guide shaft portion can be screwed-engaged in said threaded hole of said pressing member.

2. An intramedullary nail mounting instrument according to claim 1, wherein said base portion is provided with a drill guide which guides a drill that is adapted to pierce at least one preliminary hole in one of the bone pieces, corresponding to at least one threaded hole which is formed in advance in the intramedullary nail inserted in the bone pieces, said at least one threaded hole extending in a direction normal to the longitudinal direction of the intramedullary nail.

3. An intramedullary nail mounting instrument according to claim 2, wherein said drill guide is positioned such that said at least one preliminary hole is registered with the corresponding threaded hole of the intramedullary nail.

4. An intramedullary nail mounting instrument according to claim 1, wherein said pressing member moving means comprises a male member which is screw-engaged by the base portion to extend parallel to said guide shaft portion, said male member being rotatably connected at the front end thereof to said pressing member so as not to relatively move in the axial direction.

5. An intramedullary nail mounting instrument according to claim 1, wherein said base portion comprises a large diameter portion and a small diameter portion, and wherein said small diameter portion comprises said guide shaft portion.

6. An intramedullary nail mounting instrument according to claim 1, wherein said base portion has a male screw member which is screw-engaged with said base portion, and wherein said male screw member is capable of being detachably screw-engaged with the intramedullary nail.

7. An intramedullary nail inserting and mounting instrument comprising:

a base portion mountable to one end of an intramedullary nail, the intramedullary nail being inserted in the bane marrow of a pair of bone pieces of a fractured bone to be interconnected;

said base portion comprising:

a guide shaft portion extending in a longitudinal direction of the intramedullary nail;

a supporting member for supporting said guide shaft portion; and an arm;

wherein said guide shaft portion, said supporting member and said arm are integrally formed;

said guide shaft portion comprising a cylindrical member including an axial hole extending along a longitudinal direction of the intramedullary nail;

a screw member insertable in said axial hole, said screw member having a male thread to be screwed-engaged in said one end of the intramedullary nail;

a pressing member movable along said guide shaft portion to contact one end of one of the bone pieces; and means for moving said pressing member along said guide shaft portion.

8. The intramedullary nail mounting instrument according to claim 7, said arm comprising a drill guide which guides a drill that is adapted to pierce at least one preliminary hole in one of the bone pieces, corresponding to at least one threaded hole provided in the intramedullary nail inserted in the bone pieces, said at least one threaded hole extending in a direction normal to the longitudinal direction of the intramedullary nail.

9. The intramedullary nail mounting instrument according to claim 8, wherein said drill guide is positioned such that said at least one preliminary hole is registered with the corresponding threaded hole of the intramedullary nail.

10. The intramedullary nail mounting instrument according to claim 7, said pressing member moving means comprising a male member screw-engaged by said base portion to extend parallel to said guide shaft portion, said male member being rotatably connected, at a first end, to said pressing member so as not to move relative to said pressing member in the longitudinal direction of the intramedullary nail.

11. The intramedullary nail mounting instrument according to claim 7, wherein said pressing member moving means comprises a threaded portion provided on an outer peripheral surface of said guide shaft portion and a threaded hole formed in said pressing member, so that said threaded portion of said guide shaft portion can be screw-engaged in said threaded hole of said pressing member.

12. The intramedullary nail mounting instrument according to claim 7, said base portion comprising a large diameter portion and a small diameter portion, said small diameter portion comprising said guide shaft portion.

13. The intramedullary nail mounting instrument according to claim 7, said base portion comprising a male screw member screw-engaged with said base portion, said male screw member being screw-engagable with the intramedullary nail.

14. The intramedullary nail inserting and mounting instrument according to claim 7, said pressing member positioned along said guide shaft portion between said arm and an end of said screw member screw-engagable with said one end of the intramedullary nail.

15. An intramedullary nail inserting and mounting instrument comprising:

a base portion which can be mounted to one end of an intramedullary nail, the intramedullary nail inserted in a pair of bone pieces to be interconnected;

a guide shaft portion coupled to said base portion and extending in a longitudinal direction of the intramedullary nail;

a pressing member which is movable along said guide shaft portion to contact an end of one of the pair of bone pieces; and means for moving said pressing member along said guide shaft portion.

16. An intramedullary nail mounting instrument according to claim 15, wherein said base portion is provided with a drill guide which guides a drill that is adapted to pierce at least one hole in one of the bone pieces, corresponding to at least one threaded hole which is formed in the intramedullary nail inserted in the bone pieces, said at least one threaded hole extending in a direction normal to the longitudinal direction of the intramedullary nail.

17. The intramedullary nail mounting instrument according to claim 16, wherein said drill guide is positioned such that said at least one preliminary hole is registered with the corresponding threaded hole of the intramedullary nail.

18. The intramedullary nail mounting instrument according to claim 15, said pressing member moving means comprising a male member screw-engaged by said base portion to extend parallel to said guide shaft portion, said male member being rotatably connected, at a first end, to said pressing member so as not to move relative to said pressing member in the longitudinal direction of the intramedullary nail.

19. The intramedullary nail mounting instrument according to claim 15, wherein said pressing member moving means comprises a threaded portion provided on an outer peripheral surface of said guide shaft portion and a threaded hole formed in said pressing member, so that said threaded portion of said guide shaft portion can be screw-engaged in said threaded hole of said pressing member.

* * * * *

UNITED STATES PATENT AND TRADEMARK OFFICE
CERTIFICATE OF CORRECTION

PATENT NO. : 5,665,086
DATED : September 9, 1997
INVENTOR(S) : M. ITOMAN et al.

It is certified that error appears in the above-indentified patent and that said Letters Patent is hereby corrected as shown below:

In column 7, line 27 (claim 4, line 2)
        change "1" to ---7---.

In column 7, line 47 (claim 7, line 4)
        change "bane" to ---bone---.

Signed and Sealed this

Eleventh Day of August 1998

Attest:

BRUCE LEHMAN

*Attesting Officer*      *Commissioner of Patents and Trademarks*